United States Patent
Magin et al.

(10) Patent No.: US 10,048,345 B2
(45) Date of Patent: Aug. 14, 2018

(54) FRACTIONAL ORDER AND ENTROPY BIO-MARKERS FOR BIOLOGICAL TISSUE IN DIFFUSION WEIGHTED MAGNETIC RESONANCE IMAGING

(71) Applicant: The Board of Trustees of the University of Illinois, Urbana, IL (US)

(72) Inventors: Richard Magin, Western Springs, IL (US); Carson Ingo, Chicago, IL (US)

(73) Assignee: THE BOARD OF TRUSTEES OF THE UNIVERSITY OF ILLINOIS, Urbana, IL (US)

(*) Notice: Subject to any disclaimer, the term of this patent is extended or adjusted under 35 U.S.C. 154(b) by 333 days.

(21) Appl. No.: 14/772,912

(22) PCT Filed: Mar. 7, 2014

(86) PCT No.: PCT/US2014/021546
§ 371 (c)(1),
(2) Date: Sep. 4, 2015

(87) PCT Pub. No.: WO2014/138529
PCT Pub. Date: Sep. 12, 2014

(65) Prior Publication Data
US 2016/0018504 A1    Jan. 21, 2016

Related U.S. Application Data
(60) Provisional application No. 61/774,287, filed on Mar. 7, 2013.

(51) Int. Cl.
*G01R 33/48* (2006.01)
*G01R 33/563* (2006.01)
(Continued)

(52) U.S. Cl.
CPC ........ *G01R 33/56341* (2013.01); *A61B 5/055* (2013.01); *A61B 5/4064* (2013.01); *G01R 33/4818* (2013.01); *A61B 2576/00* (2013.01)

(58) Field of Classification Search
CPC ... A61B 5/055; A61B 2576/00; A61B 5/4064; G01R 33/56341; G01R 33/4818
See application file for complete search history.

(56) References Cited

FOREIGN PATENT DOCUMENTS

WO    WO2006/091983 A2 *  8/2006

OTHER PUBLICATIONS

Bennett KM, Schmainda KM, Bennett RT, Rowe DB, Lu H, Hyde JS. Characterization of continuously distributed cortical water diffusion rates with a stretched-exponential model. Magn Reson Med 2003;50:727-734.

(Continued)

*Primary Examiner* — Jay Patidar
(74) *Attorney, Agent, or Firm* — McDonnell Boehnen Hulbert & Berghoff LLP

(57) ABSTRACT

Disclosed herein is an example method and system for characterizing a biological structure in terms of bio-markers derived from diffusion weighted magnetic resonance imaging (DWI) data of biologic material. A first set of DWI data may be obtained using a fixed diffusion encoding gradient and a plurality of diffusion time resolutions, and a second set of DWI data may be obtained using a fixed diffusion time resolution and a plurality of diffusion encoding gradients. The first and second sets may be analytically fit with a fractional power-law diffusion model parameterized by fractional exponents each uniquely corresponding to one of a plurality of bio-markers of the biologic material. Fractional exponents may be determined from the analytical fitting of the first and second sets of DWI data, and an image of the biologic material may be generated and displayed.

16 Claims, 8 Drawing Sheets

(51) Int. Cl.
*A61B 5/055* (2006.01)
*A61B 5/00* (2006.01)

(56) References Cited

OTHER PUBLICATIONS

Magin RL, Abdullah O, Baleanu D, Zhou XJ. Anomalous diffusion expressed through fractional order differential operators in the Bloch-Torrey equation. J Magn Reson 2008;190:255-270.

Zhou XJ, Gao Q, Abdullah O, Magin RL. Studies of anomalous diffusion in the human brain using fractional order calculus. Magn Reson Med 2010;63:562-569.

De Santis S, Gabrielli A, Bozzali M, Maraviglia B, Macaluso E, Capuani S. Anisotropic anomalous diffusion assessed in the human brain by scalar invariant indices. Magn Reson Med 2011;65:1043-1052.

Hall MG, Barrick TR. From diffusion-weighted MRI to anomalous diffusion imaging. Magn Reson Med 2008;59:447-455.

Metzler R, Klafter J. The random walk's guide to anomalous diffusion: a fractional dynamics approach. Phys Rep 2000;339:1-77.

Palombo M, Gabrielli A, De Santis S, Cametti C, Ruocco G, Capuani S. Spatio-temporal anomalous diffusion in heterogeneous media by nuclear magnetic resonance. J Chem Phys 2011;135:034504.

Shannon CE. A mathematical theory of communication. Bell Syst Tech J 1948;27:379-423.

Viertiö-Oja H, Maja V, Sarkela M, Talja P, Tenkanen N, Tolvanen-Laakso H, Paloheimo M, Vakkuri A, Yli-Hankala A, Meriläinen P. Description of the Entropy algorithm as applied in the Datex-Ohmeda S/5 Entropy Module. Acta Anaesth Scand 2004;48:154-161.

Parekh MB, Carney PR, Sepulveda H, Norman W, King M, Mareci TH. Early MR diffusion and relaxation changes in the parahippocampal gyrus precede the onset of spontaneous seizures in an animal model of chronic limbic epilepsy. Exp Neural 2010;224:258-270.

* cited by examiner

US 10,048,345 B2

FRACTIONAL ORDER AND ENTROPY BIO-MARKERS FOR BIOLOGICAL TISSUE IN DIFFUSION WEIGHTED MAGNETIC RESONANCE IMAGING

This Application is a U.S. national phase of International Application No. PCT/US2014/021546 filed on Mar. 7, 2014, which claims the benefit of priority to U.S. Provisional Application 61/774,287 filed Mar. 7, 2013, both of which are incorporated by reference herein in their entirety.

This invention was made with government support under grant number EB007537 awarded by the National Institutes of Health. The government has certain rights in the invention.

BACKGROUND

Magnetic resonance imaging (MRI) is commonly used to image the internal tissues of a subject.

MRI is typically performed by placing the subject or object to be imaged at or near the isocenter of a strong, uniform magnetic field, $B_0$, known as the main magnetic field. The main magnetic field causes the atomic nuclei (spins) that possess a magnetic moment in the matter comprising the subject or object to become aligned in the magnetic field. The spins form a magnetization that processes around the magnetic field direction at a rate proportional to the magnetic field strength. For hydrogen nuclei (which are the common nuclei employed in MRI), the precession frequency is approximately 64 MHz in a magnetic field of 1.5 Tesla. If the magnetization is perturbed by a small radio-frequency magnetic field, known as a $B_1$ magnetic field, the spins emit radiation at a characteristic radio frequency (RF). The emitted RF radiation can be detected and analyzed to yield information that may be used to produce an image of the subject or object. For purposes of the discussion herein, the term "object" will be used to refer to either a subject (e.g., a person) or an object (e.g., a test object) when describing magnetic resonance imaging of that "object."

In practice, magnetic field gradients are also applied to the subject or object in addition to the main magnetic field. The field gradients are typically applied along one or more orthogonal axes, (x, y, z), the z-axis usually being aligned with the $B_0$, and introduce spatially-distributed variations in frequency and/or phase of the processing nuclear spins. By applying the radio-frequency $B_1$ magnetic field and gradient fields in carefully devised pulses and/or sequences of pulses that are switched on and off, the RF radiation emitted can carry spatially encoded information that, when detected and analyzed, can be used to produce detailed, high resolution images of the subject or object. Various techniques utilizing both specific pulse sequences and advanced image reconstruction methods have been developed, providing new advances, as well as introducing new challenges.

An MRI system typically includes hardware components, including a plurality of gradient coils positioned about a bore of a magnet, an RF transceiver system, and an RF switch controlled by a pulse module to transmit RF signals to and receive RF signals from an RF coil assembly. The received RF signals are also known as magnetic resonance (MR) signal data. An MRI system also typically includes a computer programmed to cause the system to apply to an object in the system various RF signals, magnetic fields, and field gradients for inducing spin excitations and spatial encoding in an object, to acquire MR signal data from the object, to process the MR signal data, and to construct an MR image of the object from the processed MR signal data. The computer can include one or more general or special purpose processors, one or more forms of memory, and one or more hardware and/or software interfaces for interacting with and/or controlling other hardware components of the MRI system.

MR signal data detected from an object are typically described in mathematical terms as "k-space" data (k-space is the 2D Fourier transform of the image). An image in actual space is produced by a Fourier transform of the k-space data. MR signal data are acquired by traversing k-space over the course of applying to the object the various RF pulses and magnetic field gradients. In practice, techniques for acquiring MR signal data from an object are closely related to techniques for applying the various RF pulses and magnetic field gradients to the object.

In diffusion weighted MRI (DWI) studies of neural tissue (e.g., human or other animal brain), a classical model assumes the statistical mechanics of Brownian motion and predicts a mono-exponential signal decay. However, some studies indicate signal decays which are not mono-exponential, particularly in the white matter. This deviation from the mono-exponential decay regime is called "anomalous diffusion." In neurodegenerative diseases, neural injuries, and neuroblastomas, the tissue microstructure in the brain is found to be altered from that of healthy neural tissue. In principle, DWI offers the non-invasive monitoring capability to measure microstructural changes via diffusion dynamics of water within the probed tissue to quantify the pathology.

In conventional DWI, a signal is modeled as the mono-exponential decay function, $\exp[-(bD)]$, where D is a classical diffusion coefficient and b is a MRI pulse sequence controlled parameter comprised of q (i.e., diffusion spatial resolution) and $\Delta$ (i.e., diffusion temporal resolution). To interpret the anomalous diffusion decay signal which is not mono-exponential, conventional techniques have been modified by applying: (1) a bi-exponential function, (e.g. $A\exp[-bD_1]+(1-A)\exp[-bD_2]$ where $A$ is a volume fraction, $D_1$ is the fast diffusion coefficient, and $D_2$ is the slow diffusion coefficient); (2) a stretched exponential function (e.g., $\exp[-(bD)^w]$, where w is the stretching parameter over the entire b value; (3) a stretched exponential function (e.g., $\exp[-(q^w\Delta D)]$, where w is the stretching parameter over the b-value component, q; and (4) a stretched exponential function (e.g., $\exp[-(q\Delta^w D)]$, where w is the stretching parameter over the b-value component, A.

Accordingly a need exists for a DWI protocol that is able to resolve diffusion patterns in neural tissue morphology, and for a comprehensive methodology for interpreting MRI anomalous diffusion decay signals.

SUMMARY

In spin-echo diffusion MRI experiments, signal decay is modeled with a mono-exponential as, $\exp(-bD)$ where b is the product of the q-space and diffusion time terms. As such, a diffusion-weighted experiment can be constructed with a set of b-values, with arbitrary weighting on the q and $\Delta$ components, so that a choice can be made to fix A and vary q in an array, or to fix q and vary A in an array.

A basic feature of Brownian motion is that the mean squared displacement (MSD) of diffusing particles grows linearly with time, $<x^2(t)>\sim t$, provided three conditions are satisfied. Specifically: (1) increments are identically distributed with finite variance; (2) increments are independent (i.e., no "memory"); and (3) the process is continuous with an initial starting value set to zero. When any one of these conditions is not met, the diffusion process is called anomalous, and the MSD grows as a power law, $<x^2(t)>\sim t^\gamma$. When $\gamma>1$, the diffusion process is "super-diffusive," and when $0<\gamma<1$, the diffusion process is "sub-diffusive." For Brownian motion, the characteristic function can be represented by a mono-exponential decay process with respect to time. Likewise, in DWI, signal decay can also be modeled as mono-exponential decay, $\exp[-(bD)]$.

One practical approach to deriving the features of Brownian motion is the random walk (RW) model. In the RW model, the random walker's motion is governed by two stochastic processes: jump length distance and waiting time (between jump lengths). When these incremental processes are governed by a finite characteristic waiting time and jump length variance, in the continuum limit, the diffusion equation naturally arises (i.e., Fick's 2nd law). A generalization to the RW model can be obtained in the form of a continuous time random walk (CTRW) model, in which the incremental processes are no longer constrained by a Gaussian or Poissonian probability distribution function (pdf). Rather, the jump lengths and waiting times are governed by arbitrary and independent pdfs. In the most general case, the random walker's motion is represented with fractional powers on the waiting time and jump length intervals, respectively. In this case, the MSD can be represented as a power law, $<x^2(t)>\sim t^{2\alpha/\beta}$, where $0<\alpha<1$, and $0<\beta<2$. When $\alpha=1$ and $\beta=2$, the process returns to normal diffusion. When $2\alpha/\beta>1$, the process becomes "super-diffusion." When $0<2\alpha/\beta<1$, the process becomes "sub-diffusion." Solving the CTRW in the continuum limit yields a characteristic decay process that is represented by the Mittag-Leffler function (MLF), $E_\alpha(D_{\alpha,\beta} q^\beta \Delta^\alpha)$, where $D_{\alpha,\beta}$ is the diffusion coefficient with units space$^\beta$/time$^\alpha$. The MLF model is of interest because it relaxes a priori assumptions about the governing statistics of the diffusion process, and can identify normal, sub-, and super-diffusion regimes.

However, the MLF poses difficulties in practical implementation since the diffusion coefficient, $D_{\alpha,\beta}$, has fractional space and time units that are not necessarily directly measurable. Accordingly, to overcome this problem, example embodiments disclosed herein introduce a recast but equivalent form of the MLF model, expressed as $E_\alpha(D_{1,2}\tau^{1-\alpha}/\mu^{2-\beta} q^\beta \Delta^\alpha)$, in which $D_{1,2}$ is a diffusion coefficient having measurable units (e.g., mm$^2$/sec), made possible through parameters $\tau$ and $\mu$. The coefficient $D_{1,2}$ is referred to herein as a "measurable diffusion coefficient."

More particularly, example embodiments herein provide two classes of DWI protocols (hereinafter "fixed $\Delta$ protocol" and "fixed q protocol") for operating an MRI system to obtain DWI data. Example embodiments herein further include techniques for fitting the recast MLF model to data obtained in DWI acquisitions according to the fixed $\Delta$ and fixed q protocols, in order to determine bio-markers derived from the recast MLF model.

Hence, in one aspect, various embodiments of the present invention provide a computer-implemented method for characterizing a biological structure, the method comprising: acquiring a first set of diffusion weighted MRI (DWI) data of biologic material, the first set of DWI data having been measured by a magnetic resonance imaging (MRI) system using a fixed diffusion encoding gradient and a plurality of diffusion time resolutions; acquiring a second set of DWI data of the biologic material, the second set of DWI data having been measured by the MRI system using a fixed diffusion time resolution and a plurality of diffusion encoding gradients; analytically fitting the first and second sets of DWI data with a fractional power-law diffusion model parameterized by fractional exponents each uniquely corresponding to one of a plurality of bio-markers of the biologic material; determining values of the fractional exponents from the analytical fitting of the first and second sets of DWI data; and generating and displaying at least one image of the biologic material as represented by at least one of the plurality of bio-markers based on the determined values of the uniquely corresponding fractional exponent.

In another aspect, various embodiments of the present invention provide, in a magnetic resonance imaging (MRI) system, a method for characterizing a biological structure, the method comprising: acquiring a first set of diffusion weighted MRI (DWI) data of biologic material with the MRI system using a fixed diffusion encoding gradient and a plurality of diffusion time resolutions; acquiring a second set of DWI data of the biologic material with the MRI system using a fixed diffusion time resolution and a plurality of diffusion encoding gradients; analytically fitting the first and second sets of DWI data with a fractional power-law diffusion model parameterized by fractional exponents each uniquely corresponding to one of a plurality of bio-markers of the biologic material; determining values of the fractional exponents from the analytical fitting of the first and second sets of DWI data; and generating and displaying at least one image of the biologic material as represented by at least one of the plurality of bio-markers based on the determined values of the uniquely corresponding fractional exponent.

In a further aspect, various embodiments of the present invention provide a system comprising: one or more processors; memory; and machine-readable instructions stored in the memory that, when executed by the one or more processors, cause the system to carry out functions including: acquiring a first set of diffusion weighted MRI (DWI) data of biologic material, wherein the first set of DWI data comprise measurements made by a magnetic resonance imaging (MRI) system using a fixed diffusion encoding gradient and a plurality of diffusion time resolutions; acquiring a second set of DWI data of the biologic material, wherein the second set of DWI data comprise measurements made by the MRI system using a fixed diffusion time resolution and a plurality of diffusion encoding gradients; analytically fitting the first and second sets of DWI data with a fractional power-law diffusion model parameterized by fractional exponents each uniquely corresponding to one of a plurality of bio-markers of the biologic material; determining values of the fractional exponents from the analytical fitting of the first and second sets of DWI data; and generating and displaying at least one image of the biologic material as represented by at least one of the plurality of bio-markers based on the determined values of the uniquely corresponding fractional exponent.

In yet another aspect, various embodiments of the present invention a magnetic resonance imaging (MRI) system comprising: one or more processors; memory; a main magnet; one or more gradient coils; and machine-readable instructions stored in the memory that, when executed by the one or more processors, cause the MRI system to carry out functions including: acquiring a first set of diffusion weighted MRI (DWI) data of biologic material in the MRI system using a fixed diffusion encoding gradient and a plurality of diffusion time resolutions, acquiring a second set of DWI data of the biologic material in the MRI system using a fixed diffusion time resolution and a plurality of diffusion encoding gradients; analytically fitting the first and second sets of DWI data with a fractional power-law diffusion model parameterized by fractional exponents each uniquely corresponding to one of a plurality of bio-markers of the biologic material, determining values of the fractional exponents from the analytical fitting of the first and second sets of DWI data, and generating and displaying at least one image of the biologic material as represented by at least one of the plurality of bio-markers based on the determined values of the uniquely corresponding fractional exponent.

In accordance with example embodiments, the DWI bio-markers can be used to identify regimes of sub-, super-, and normal diffusion in neural tissue.

In further accordance with example embodiments, the DWI bio-markers can be used to distinguish healthy neural tissue from degenerated or injured neural tissue.

In accordance with example embodiments, the fixed Δ protocol can be used to identify anomalous diffusion in white matter and gray matter regions in healthy, degenerated, and injured neural tissue.

In accordance with example embodiments, the fixed q protocol can be used to identify anomalous diffusion, different from that identified in the fixed Δ protocol, in white matter and gray matter regions in healthy, degenerated, and injured neural tissue.

These as well as other aspects, advantages, and alternatives will become apparent to those of ordinary skill in the art by reading the following detailed description, with reference where appropriate to the accompanying drawings. Further, it should be understood that this summary and other descriptions and figures provided herein are intended to illustrate the invention by way of example only and, as such, that numerous variations are possible.

DETAILED DESCRIPTION

1. Overview

Example embodiments of the disclosed invention provide a methodology for characterizing a biological structure in terms of bio-markers derived from DWI data. The methodology includes estimating bio-markers in a fixed diffusion time protocol, estimating bio-markers in fixed diffusion encoding gradient strength protocol, calculating parameters of a model, and using the parameters to characterize a biological structure. Using the techniques and methods described herein, the data may be used to identify structural degeneration, structural integrity and response to therapeutics.

More particularly, example embodiments herein provide a "fixed Δ protocol" DWI protocol and a "fixed q protocol" DWI protocol for operating an MRI system to obtain DWI data. In example embodiments, a fixed Δ protocol can provide Δ fixed at a value in a range of 15-100 ms, and a q value array set in a range of 0-200 $mm^{-1}$, corresponding to gradient strengths of 0-1500 mT/m. Example embodiments can further provide a fixed q protocol, in which q can be fixed at a value in a range of 15-100 $mm^{-1}$, corresponding to gradient strengths of 100-1000 mT/m, and a Δ value array can be set in a range of 15-250 ms. Example embodiments herein further provide DWI bio-markers for neural morphology, which are processed from the fixed Δ protocol and fixed q protocol DWI data. As described below, the bio-markers correspond to the parameters $\alpha$, $\beta$, $D_{1,2}$, $\mu$, $\tau$ of the recast MLF model introduced above, as well as an entropy H derived from the parameters. The techniques discussed herein can be adapted for application to other biologic material besides neural tissue.

Figure 1:
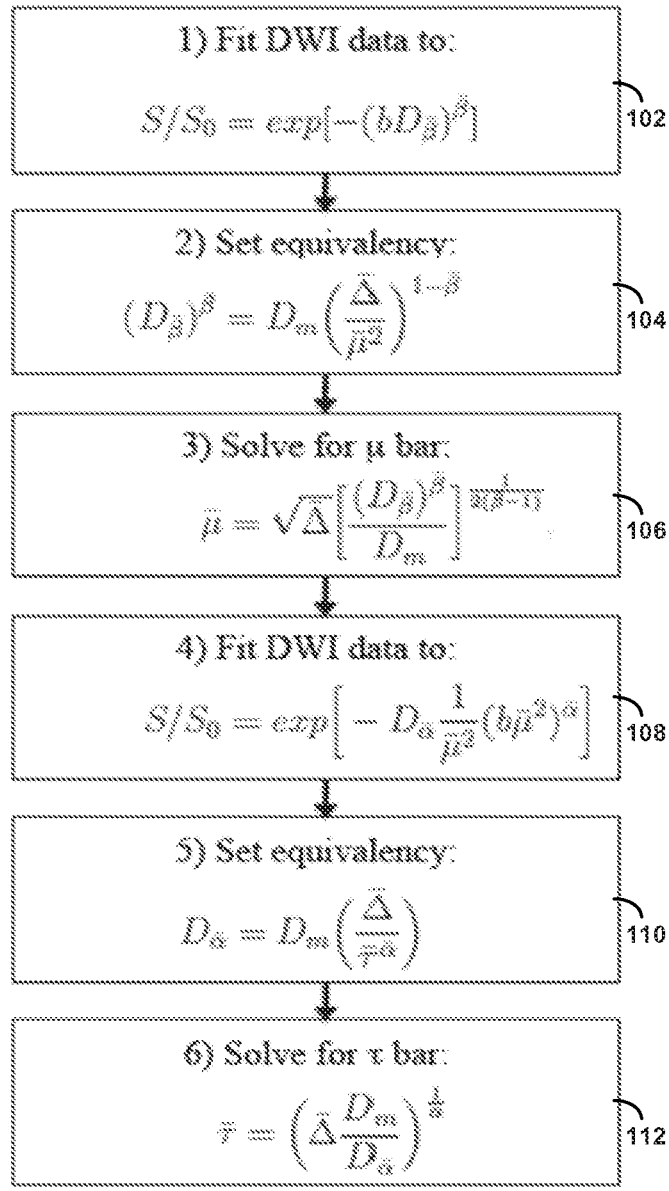
FIG. 1 is a flowchart illustrating a first estimation of model parameters, in accordance with example embodiments.
Figure 2:
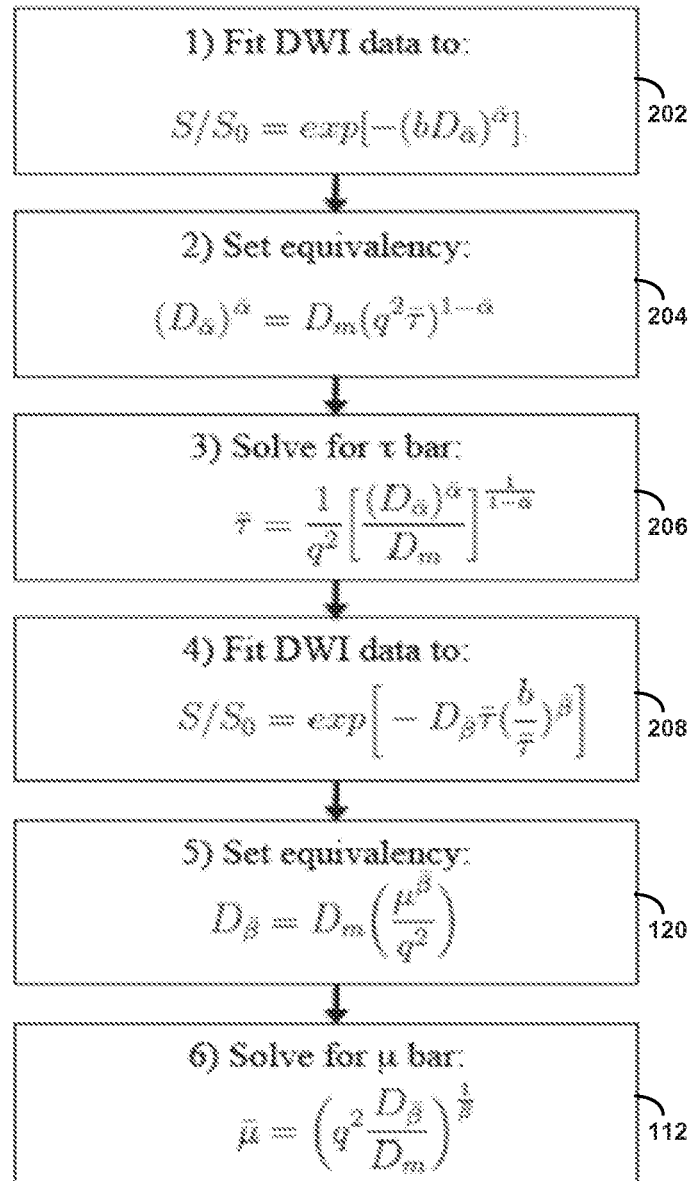
FIG. 2 is a flowchart illustrating a second estimation of model parameters, in accordance with example embodiments.

To determine $D_{1,2}$, an "estimated measureable diffusion coefficient," $D_m$, is first obtained by fitting a mono-exponential function to the first three low b-value samples. After $D_m$ has been obtained, two analogous stretched exponential fitting procedures are used to fit the fixed Δ protocol and fixed q protocol DWI data in order to find estimates of μ and τ, the estimated parameters denoted as f̄t and f̄ bar. The forms of the two analogous stretched exponential functions utilize the diffusion experiment pulse sequence parameters in order to independently constrain the magnitudes of f̄f and f̄ bar. Example flowcharts of the fitting procedures are shown in FIGS. 1 and 2. In order to fit the MLF, $D_m$, $\bar{\mu}$, $\bar{\tau}$, and $\alpha=1$, $\beta=2$ are used as starting values in order to converge upon values of $D_{1,2}$, μ, τ, α, and β.

As indicated in FIG. 1, $\bar{\mu}$ and $\bar{\tau}$ are estimated using DWI data acquired according to the fixed Δ protocol. At step 102, the DWI data are fit with a stretched exponential expressed as $S/S_0 = \exp[(bD_{\bar{\beta}})^{\bar{\beta}}]$.

At step 104, an equivalency is set according to $$(D_{\bar{\beta}})^{\bar{\beta}} = D_m \left(\frac{\Delta}{\bar{\mu}^2}\right)^{1-\bar{\beta}}.$$

At step 106, a solution for f̄t is derived according to $$\bar{\mu} = \sqrt{\Delta} \left[\frac{(D_{\bar{\beta}})^{\bar{\beta}}}{D_m}\right]^{\frac{1}{2(\bar{\beta}-1)}}.$$

At step 108, the DWI data are fit with an exponential $$S/S_0 = \exp\left[-D_{\bar{\alpha}} \frac{1}{\bar{\mu}^2}(b\bar{\mu}^2)^{\bar{\alpha}}\right].$$

At step 110, an equivalency is set according to $$D_{\bar{\alpha}} = D_m\left(\frac{\Delta}{\bar{\tau}^{\bar{\alpha}}}\right).$$

Finally, at step 112, a solution for $\bar{\tau}$ is derived according to $$\tau = \left(\Delta \frac{D_m}{D_\alpha}\right)^{\frac{1}{\alpha}}.$$

FIG. 2 illustrates estimation of $\bar{\tau}$ and $\bar{\mu}$ using DWI data acquired according to the fixed q protocol. At step 202, the DWI data are fit with a stretched exponential expressed as $S/S_0 = \exp[-(bD_{\bar{\alpha}})^{\bar{\alpha}}]$.

At step 204, an equivalency is set according to $(D_{\bar{\alpha}})^{\bar{\alpha}} = D_m(q^2\tau)^{1-\bar{\alpha}}$.

At step 206, a solution for $\bar{\tau}$ is derived according to $$\bar{\mu} = \frac{1}{q^2}\left[\frac{(D_\alpha)^\alpha}{D_m}\right]^{\frac{1}{1-\alpha}}.$$

At step 208, the DWI data are fit with an exponential $$S/S_0 = \exp\left[-D_{\bar{\beta}}\tau\left(\frac{b}{\tau}\right)^{\bar{\beta}}\right].$$

At step 210, an equivalency is set according to $$D_{\bar{\beta}} = D_m\left(\frac{\mu^{\bar{\beta}}}{q^2}\right).$$

Finally, at step 212, a solution for $\bar{\tau}$ is derived according to $$\bar{\mu} = \left(q^2 \frac{D_{\bar{\beta}}}{D_m}\right)^{\frac{1}{\bar{\beta}}}.$$

In information theory, the amount of uncertainty in a stochastic process can be measured with Shannon information entropy (Shannon, "A mathematical theory of communication," Bell System Tech. Journal, 27:379-423, 1948). Considering information formulated in the context of statistical uncertainty can therefore provide tool to compare systems governed by differing stochastic processes, and their corresponding pdfs. For example, when comparing two alpha stable distributions, the Gaussian and the Cauchy, normalized with the same full-width, half maximum values, the Cauchy distribution can be shown to have greater information entropy. Non-Gaussian, or anomalous, diffusion phenomena have been correlated to regions of increased tissue complexity, such as white matter in the brain, which is relatively more anisotropic, heterogeneous, and tortuous compared to gray matter regions. From the information theory perspective, the white matter regions can thus be considered to have greater entropy than the gray matter regions, as they are governed by more uncertain diffusion pdfs.

Another approach to measure the uncertainty in a system is to analyze the characteristic function in terms of the Fourier transform in space with spectral entropy. Accordingly, example embodiments disclosed herein provide an entropy formalism for b-value diffusion decay signals as a function of q and $\Delta$. The formalism derives from the MLF as a measure of the uncertainty of a characteristic function. As described below, after the MLF parameters are determined, a characteristic decay curve is reconstructed over the b-value range in either the fixed $\Delta$ protocol or fixed q protocol and the entropy in the diffusion process is computed as $H(q,\Delta)$.

Demonstration studies of the techniques provided in accordance with example embodiments disclosed herein were carried out using rat brains as test specimens of biologic material. More particularly, the fixed q and fixed $\Delta$ protocols were applied to acquisition of DWI data for a healthy rat brain and an epileptic rat brain. A brief summary of the results is presented below.

Application of the techniques provided in accordance with example embodiments is illustrated in Table 1, which shows that a separates the cerebral cortex, the central corpus callosum, and the striatum. In the fixed q protocol, a distinguishes the central corpus callosum from the lateral corpus callosum. In general, $\beta$ shows less contrast than a and for the regions containing gray matter, $\beta\sim2$, indicating Gaussian statistics on the jump length distributions. However, in the fixed $\Delta$ protocol, $\beta$ separates the central corpus callosum from the regions containing gray matter. In the fixed $\Delta$ protocol, the measurable diffusion coefficient, $D_{1,2}$, separates the central corpus callosum from the striatum. In the fixed q protocol, $\mu$ separates the central corpus callosum from the regions containing gray matter. In the fixed $\Delta$ and fixed q protocols, $\tau$ separates the central corpus callosum from the regions containing gray matter. Numerical values for DWI MLF parameters in Table 1 are as follows: in the fixed $\Delta$ protocols, $\Delta_1=17.5$ ms and $\Delta_2=50$ ms, and fixed q protocols, $q_1=78$ mm$^{-1}$ and $q_2=52$ mm$^{-1}$, on an axial slice through a healthy rat brain using a diffusion weighted stimulated echo pulse sequence.

Figure 3:
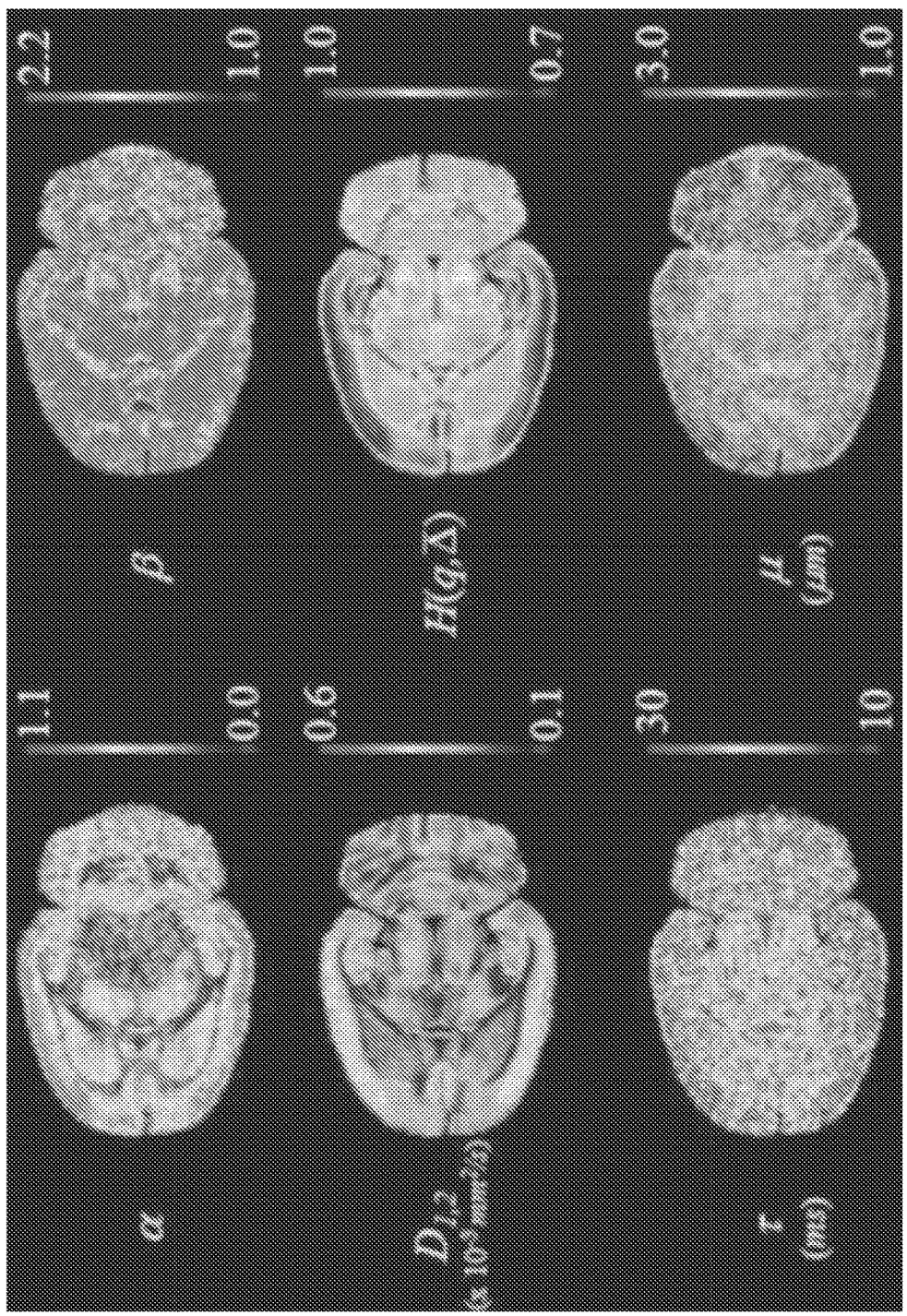
FIG. 3 illustrates a first example of DWI parameter maps of a rat brain, in accordance with example embodiments.
Figure 4:
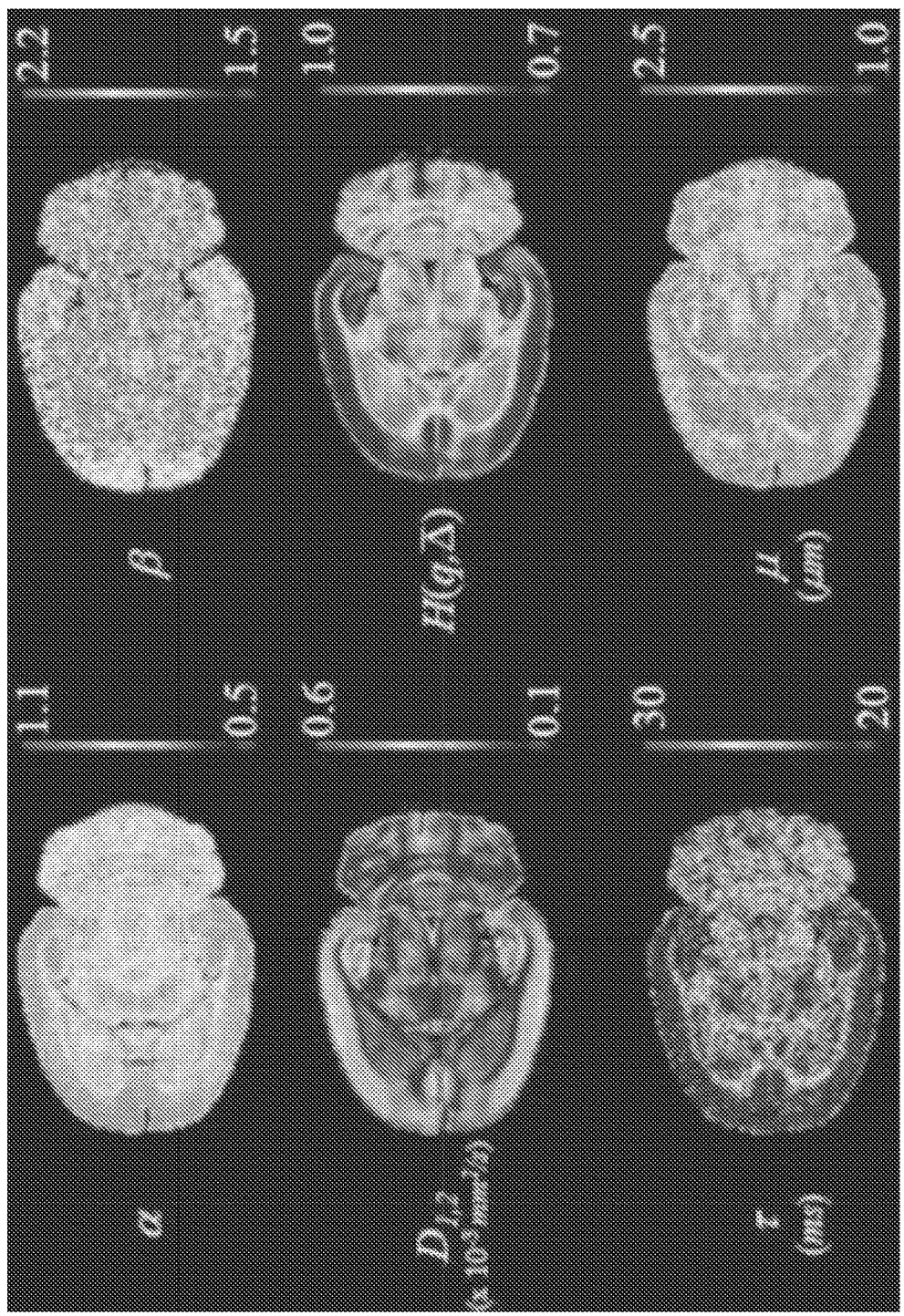
FIG. 4 illustrates a second example of DWI parameter maps of a rat brain, in accordance with example embodiments.

Region of interest (ROI) analysis can be extended across the entire brain slice, which, by way of example, is represented as parameter maps in FIGS. 3-4. Specifically, FIG. 3 illustrates DWI parameter maps for the fixed $\Delta$ protocol, $\Delta=17.5$ ms, on an axial slice through a healthy rat brain using a diffusion-weighted stimulated echo pulse sequence. FIG. 4 illustrates DWI parameter maps for the fixed q protocol, $q=78$ mm$^{-1}$, on an axial slice through a healthy rat brain, on an axial slice through a healthy rat brain using a diffusion weighted stimulated echo pulse sequence.

Further application of the techniques is illustrated in Table 2, which shows that the entropy, $H(q,\Delta)$, in the MLF distinguishes the central corpus callosum from the lateral white matter. In the fixed $\Delta$ and q protocols, $H(q,\Delta)$ separates the cerebral cortex, the central corpus callosum, and the striatum. For comparison, the entropy, $H(q,\Delta)$ of the mono-exponential is shown in Table 2 to demonstrate the increased information provided in the MLF about the ROI. Numerical values for DWI entropy parameters in Table are as follows: in the fixed $\Delta$ protocols, $\Delta_1=17.5$ ms and $\Delta_2=50$ ms, and fixed q protocols, $q_1=78$ mm$^{-1}$ and $q_2=52$ mm$^{-1}$, on an axial slice through a healthy rat brain using a diffusion weighted stimulated echo pulse sequence. The top row shows the contrast in the neural tissue produced by the MLF. The bottom row shows the contrast in the neural tissue produced by the mono-exponential function.

Figure 5:
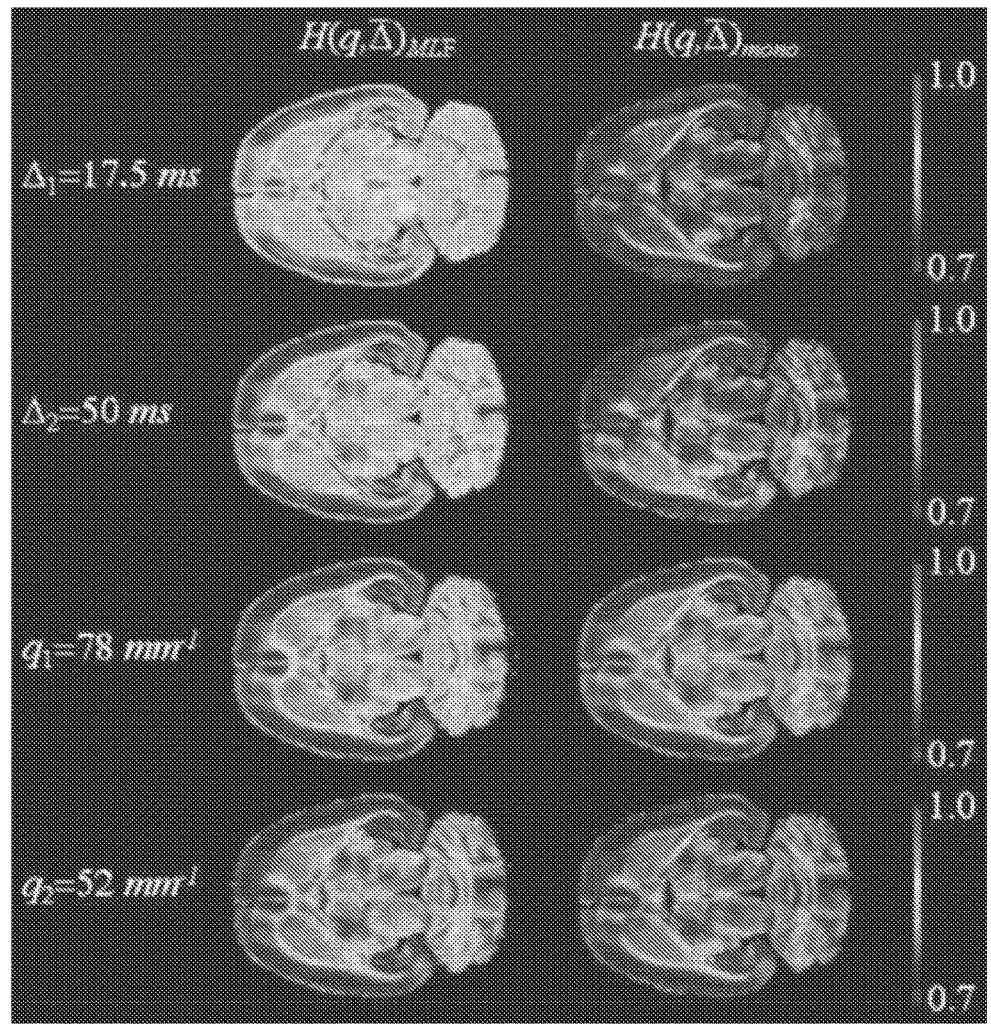
FIG. 5 illustrates a third example of DWI parameter maps of a rat brain, in accordance with example embodiments.

Further ROI analysis is extended across the entire brain slice, which is represented as parameter maps in FIG. 5. More particularly, FIG. 5 illustrates DWI entropy maps for the fixed $\Delta$ protocols, $\Delta_1=17.5$ ms and $\Delta_2=50$ ms, and fixed q protocols, $q_1=78$ mm$^{-1}$ and $q_2=52$ mm$^{-1}$, on an axial slice through a healthy rat brain using a diffusion weighted stimulated echo pulse sequence. The left column shows the image contrast in the neural tissue produced by the MLF. The right column shows the image contrast in the neural tissue produced by the mono-exponential function.

Table 3 shows the ratio, $2\alpha/\beta$ as the composite exponent in the context of the trajectory of the MSD. In the fixed $\Delta$ protocol, all ROIs indicated sub-diffusion ($2\alpha/\beta<1$), with the lateral corpus callosum regions growing slowest with respect to time. In the fixed $\Delta$ protocol, the corpus callosum ROIs are most sub-diffusive, whereas the cortex and striatum show slight sub-diffusion and effective normal diffusion ($2\alpha/\beta\sim1$). In the fixed q protocol, the central corpus callosum ROI is most sub-diffusive, whereas the cortex and striatum show slight sub-diffusion and effective normal diffusion. Numerical values for DWI MLF parameter, $2\alpha/\beta$, in Table 3 are as follows: in the fixed $\Delta$ protocols, $\Delta_1$=17.5 ms and $\Delta_2$=50 ms, and fixed q protocols, $q_1$=78 $mm^{-1}$ and $q_2$=52 $mm^{-1}$, on an axial slice through a healthy rat brain using a diffusion weighted stimulated echo pulse sequence.

Table 4 shows mean and standard deviation of the DWI MLF and entropy parameters for the fornix (F) ROIs in healthy and epileptic rat brains in the fixed $\Delta$ protocol, $\Delta$=17.5 ms.

Figure 6:
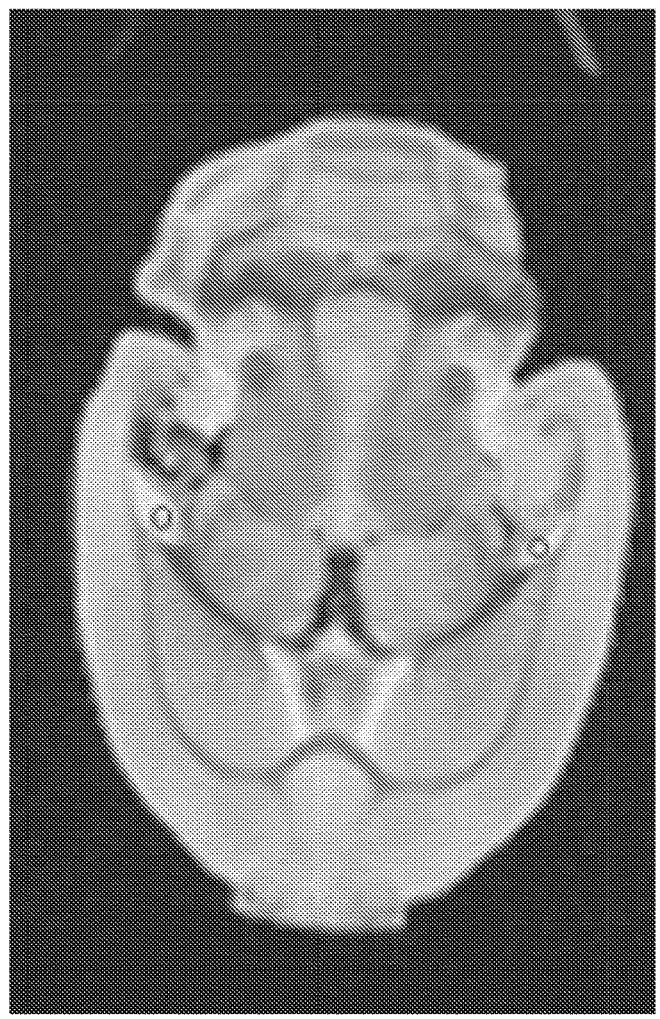
FIG. 6 illustrates example DWI parameter maps of an epileptic rat brain, in accordance with example embodiments.

FIG. 6 shows a T2 weighted image of an age matched epileptic rat brain, with the lateral fornix ROIs circled in black. The fornix has been reported to significantly change in diffusion tensor imaging studies with a fractional anisotropy reduced by ~15% in epilepsy compared to healthy. Table 3 shows a comparison of fornix ROIs in healthy versus epileptic rat brains using the MLF and entropy parameters. There is a change in the MLF parameters, especially when considering the composite ratio in the power law growth of the mean-squared displacement, $2\alpha/\beta$ in which the healthy tissue is highly sub-diffusive ($2\alpha/\beta\sim0.24$-$0.33$) and the degenerated tissue approaches Brownian motion ($2\alpha/\beta\sim0.88$-$0.89$). Overall, this change is encoded with entropy, $H(q, \Delta)$, as a drastic loss of information in the tissue structure going from healthy ($H(q, \Delta)\sim0.90$-$0.91$) to epileptic ($H(q, \Delta)\sim0.54$-$0.56$).

It should be noted that various changes and modifications to the presently preferred embodiments described herein will be apparent to those skilled in the art. Such changes and modifications may be made without departing from the spirit and scope of the present invention and without diminishing its attendant advantages.

2. Example Methods

Embodiments disclosed herein by way of example of fractional order and entropy bio-markers in DWI provide example techniques applicable in an MRI system or in a computer system at which DWI data can be accessed. As described above, an MRI system typically comprises hardware components including one or more gradient coils positioned about a bore of a magnet, an RF transceiver system, and an RF switch controlled by a pulse module to transmit RF signals to and receive RF signals from an RF coil assembly. The received RF signals are also known as magnetic resonance (MR) signal data. An MRI system also typically includes one or more computers programmed to cause the system to apply to an object in the system various RF signals, magnetic fields, and field gradients for inducing spin excitations and spatial encoding in an object, to acquire MR signal data from the object, to process the MR signal data, and to construct an MR image of the object from the processed MR signal data. The one or more computers can include one or more general or special purpose processors, one or more forms of memory, and one or more hardware and/or software interfaces for interacting with and/or controlling other hardware components of the MRI system.

Figure 7:
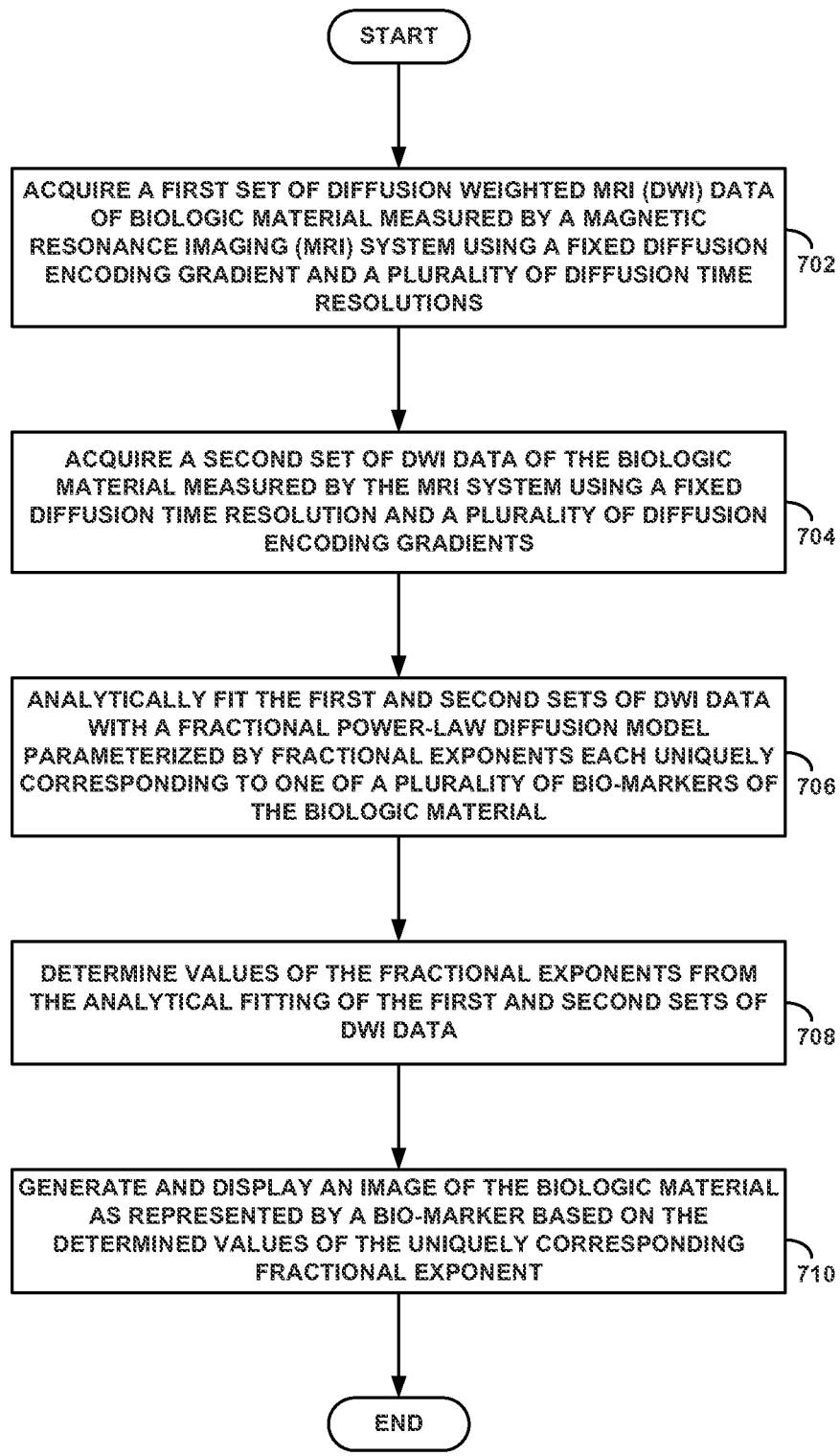
FIG. 7 is a flowchart illustrating an example method, in accordance with example embodiments.

In example embodiments, fractional order and entropy bio-markers from DWI data can be determined by way of a computer-implemented method configured for execution by an MRI system or in a computer system at which DWI data can be accessed. The steps of the FIG. 7 is a flowchart illustrating an example method in a computer system of determining fractional order and entropy bio-markers from DWI data.

At step 702, a first set of diffusion weighted MRI (DWI) data of biologic material is acquired. The first set of DWI data corresponds to data measured by a magnetic resonance imaging (MRI) system using a fixed diffusion encoding gradient and a plurality of diffusion time resolutions.

At step 704, a second set of DWI data of the biologic material is acquired. The second set of DWI data corresponds to measured by the MRI system using a fixed diffusion time resolution and a plurality of diffusion encoding gradients.

At step 706, the first and second sets of DWI data are analytically fit with a fractional power-law diffusion model parameterized by fractional exponents that each uniquely corresponding to one of a plurality of bio-markers of the biologic material.

At step 708, values of the fractional exponents are determined from the analytical fitting of the first and second sets of DWI data.

Finally, at step 710 at least one image of the biologic material is generated and displayed. In the image the biologic material is represented by at least one of the plurality of bio-markers based on the determine values of the uniquely corresponding fractional exponent. FIGS. 3-6 are examples of images representing a rat brain in one or another of the bio-markers described above.

In accordance with example embodiments, acquiring the first set of DWI data of the biologic material could entail acquiring the first set of DWI data from DWI data previously measured and provided for storage by the MRI system. Similarly, acquiring the second set of DWI data of the biologic material could entail acquiring the first set of DWI data from the DWI data previously measured and provided for storage by the MRI system. For example, the first and second sets of DWI data could be retrieved from an archive.

In accordance with example embodiments, the fixed diffusion encoding gradient and the plurality of diffusion time resolutions could correspond to DWI data measured using a diffusion spatial resolution with a value fixed in a range of 15 $mm^{-1}$-100 $mm^{-1}$, and an array of diffusion temporal resolution values in a range of 15 ms-250 ms. The diffusion spatial resolution range could correspond to a range of gradient strengths of 100 mT/m-1000 mT/m.

In accordance with example embodiments, the fixed diffusion time resolution and the plurality of diffusion encoding gradients could correspond to DWI data measured using a diffusion temporal resolution with a value fixed in a range of 15 ms-100 ms, and an array of diffusion spatial resolution values a range of 0 $mm^{-1}$-200 $mm^{-1}$. The diffusion spatial resolution range could correspond to corresponding to a range of gradient strengths of 0 mT/m-1500 mT/m.

In accordance with example embodiments, the fractional power-law diffusion model could include a mean square displacement (MSD) of a power-law form $<x^2(t)>\sim t^{2\alpha/\beta}$, and has a solution expressed analytically as:

$$E_\alpha\left(\frac{D_{1,2}\tau^{1-\alpha}}{\mu^{2-\beta}}q^\beta\Delta^\alpha\right),$$

$\alpha$, $\beta$, $\mu$, and $\tau$ are model parameters corresponding to four of the bio-markers, $D_{1,2}$ is a measurable diffusion coefficient corresponding to a fifth bio-marker, $E_\alpha$ is a Mittag-Leffler function (MLF), and q is the diffusion spatial resolution, and $\Delta$ is the diffusion temporal resolution. As discussed in connection with Equation (13) below, a mono-exponential model of signal decay in DWI can be expressed analytically as:

$$\frac{S}{S_0} = \exp(-bD),$$

and a stretched exponential model of signal decay in DWI is expressed analytically as:

$$\frac{S}{S_0} = \exp[-(bD)^w].$$

In these expressions, $S_0$ corresponds to an initial signal and S corresponds to a decaying signal, $b=q^2(\Delta-\delta/3)$, where $\Delta$ is the separation between gradient pulses of duration $\delta$, and D is a classical diffusion coefficient. In the stretched exponential, w is a stretching parameter.

With these definitions, analytically fitting the first and second sets of DWI data with the fractional power-law diffusion model could entail first determining an estimated measurable diffusion coefficient $D_m$ by analytically fitting a subset of the first and second sets of DWI data with a mono-exponential model of signal decay, then determining estimated values of $\mu$ and $\tau$, $\bar{\mu}$ and $\bar{\tau}$, respectively, by (i) analytically fitting the first set of DWI data with a stretched exponential model of signal decay and $w=\alpha$, and (ii) analytically fitting the second set of DWI data with a stretched exponential model of signal decay and $w=\beta$, and finally determining $D_{1,2}$, $\alpha$, $\beta$, $\mu$, and $\tau$ by iteratively fitting the first and second sets of DWI data with the fractional power-law diffusion model using $D_m$, $\bar{\mu}$, $\bar{\tau}$, $\alpha=1$, and $\beta=2$ as starting values. These operations are illustrated by way of example in FIGS. 1 and 2, a discussed above.

In further accordance with example embodiments, the power law $\langle x^2(t)\rangle \sim t^{2\alpha/\beta}$ MSD of the fractional power-law diffusion model could be derived from a random walk (RW) model characterized by stochastic processes for jump-length distance and time between jumps. In general the stochastic processes can have independent probability density functions (pdfs). The example method could then further include determining an entropy $H(q, \Delta)$ as a measure of uncertainty in the pdfs, the entropy $H(q, \Delta)$ being a sixth bio-marker.

In accordance with example embodiments, the biologic material could be neural tissue, such as a human brain.

Figure 8:
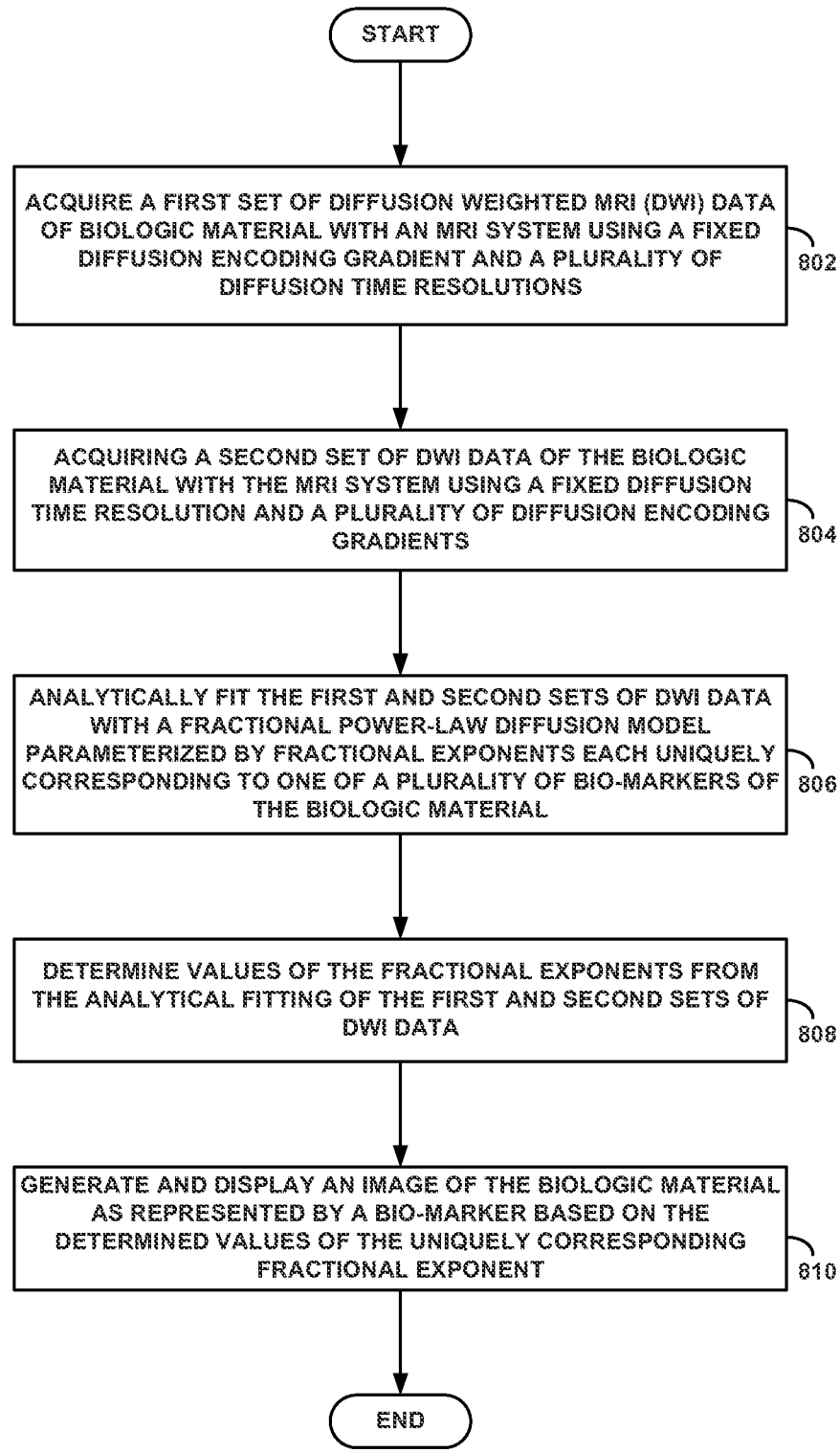
FIG. 8 is a flowchart illustrating another example method, in accordance with example embodiments.

FIG. 8 is a flowchart illustrating an example method in an MRI system of determining fractional order and entropy bio-markers from DWI data. As noted in the discussion of the method illustrated in FIG. 7, acquisition of the first and second sets of DWI data at steps 702 and 704 could entail accessing archived DWI data. The example method illustrated in FIG. 8 differs in that both DWI data acquisition and the subsequent data analysis operations (including generating and displaying the images) are carried out by the MRI system. DWI data acquisition by the MRI system is made explicit in steps 802 and 804 below. Other than these two steps, steps 806-810 are the same as step 706-710 in the example method of FIG. 7.

At step 802, a first set of diffusion weighted MRI (DWI) data of biologic material is acquired with an MRI system using a fixed diffusion encoding gradient and a plurality of diffusion time resolutions.

At step 804, a second set of DWI data of the biologic material is acquired with the MRI system using a fixed diffusion time resolution and a plurality of diffusion encoding gradients.

At step 806, the first and second sets of DWI data are analytically fit with a fractional power-law diffusion model parameterized by fractional exponents that each uniquely corresponding to one of a plurality of bio-markers of the biologic material.

At step 808, values of the fractional exponents are determined from the analytical fitting of the first and second sets of DWI data.

Finally, at step 810 at least one image of the biologic material is generated and displayed. In the image the biologic material is represented by at least one of the plurality of bio-markers based on the determine values of the uniquely corresponding fractional exponent. Again, FIGS. 3-6 are examples of images representing a rat brain in one or another of the bio-markers described above.

It will be appreciated that the example method steps of the example embodiment of method of determining fractional order and entropy bio-markers from DWI data can be embodied as executable instructions stored on a non-transitory computer-readable medium, such as magnetic disk, CD-ROM, or the like. It will also be appreciated that the method steps described above can be modified or rearranged, and that additional steps can be added, without changing the scope or spirit of example embodiments herein.

3. Example Analytical Description

Without being limited to any theory of the underlying basis for the invention one of ordinary skill will appreciate the following features of the DWI methods set forth herein.

As noted above, diffusion decay processes can deviate from the mono-exponential model. The random walk (RW) model is a practical approach to derive the features of Brownian motion. In the RW model, the random walker's motion is governed by two stochastic processes: jump length distance, $\Delta x$, and waiting time (between jump lengths), $\Delta t$. When these incremental processes are governed by a finite characteristic waiting time and jump length variance, in the continuum limit as $\Delta x \to 0$ and $\Delta t \to 0$, the diffusion equation naturally arises (i.e., Fick's $2^{nd}$). A generalization to the RW model is the continuous time random walk (CTRW) model in which the incremental processes are no longer constrained by a Gaussian or Poissonian probability distribution function (pdf). Rather, the jump lengths and waiting times are governed by arbitrary and independent pdfs. In the most general case, the random walker's motion is represented with fractional powers $\alpha$ and $\beta$ on the waiting time and jump length intervals, respectively, such that the MSD can be represented as a power law, $$\langle x^2(t)\rangle \sim t^{2\alpha/\beta}, \quad (1)$$

where $0<\alpha\leq 1$ and $0<\beta\leq 2$. When $2\alpha/\beta=1$, the process is normal diffusion. When $2\alpha/\beta>1$, the process is "super-diffusion." When $0<2\alpha/\beta<1$, the process is "sub-diffusion." Solving the CTRW in the continuum limit yields a characteristic decay process that is represented by the Mittag-Leffler function (MLF). The MLF model is attractive in that it does not make a priori assumptions about the governing statistics of the diffusion process.

From RWs to CTRWs

In the context of RW theory in which the jump length variances and characteristic waiting times are finite, the one-dimensional Brownian motion of a diffusing particle, $P(x,t)$, in homogeneous and isotropic geometries can be described according to the second order partial differential equation, $$\frac{\partial P(x,t)}{\partial t} = D \frac{\partial^2 P(x,t)}{\partial |x|^2}, \tag{2}$$

where D is the diffusion coefficient. The solution to Equation (2) follows as the familiar Gaussian form, $$P(x,t) = \frac{1}{\sqrt{4\pi Dt}} \exp\left(-\frac{x^2}{4\pi D}\right). \tag{3}$$

However, in the context of CTRW theory in which the jump length variances and characteristic waiting times follow asymptotic power law distributions, the one dimensional anomalous motion of a diffusing particle, $P(x,t)$, in heterogeneous biological tissues characterized by tortuous and porous geometries, can be described with a fractional partial differential equation of the form, $$_0^C\mathcal{D}_t^\alpha(P(x,t)) = D_{\alpha,\beta} \frac{\partial^\beta P(x,t)}{\partial |x|^\beta}, \tag{4}$$

where $_0^C\mathcal{D}_t^\alpha$ is the $\alpha^{th}$ ($0<\alpha\le 1$) fractional order time derivative in the Caputo form, $\partial^\beta/\partial|x|^\beta$ is the $\beta^{th}$ ($0<\beta\le 2$) fractional order space derivative in the Reisz form, and $D_{\alpha,\beta}$ is the effective diffusion coefficient (e.g. $mm^\beta/s^\alpha$). The closed form solution of Equation (4) can be given in the Fox's H function, $$P(x,t) = \frac{1}{\beta|x|} H_{3,3}^{2,1}\left[\frac{-|x|}{D_{\alpha,\beta}^{\frac{1}{\beta}}t^{\frac{\alpha}{\beta}}} \middle| \begin{array}{ccc}(1,\frac{1}{\beta}) & (\alpha,\frac{\alpha}{\beta}) & (1,\frac{1}{2}) \\ (1,1) & (1,\frac{1}{\beta}) & (1,\frac{1}{2})\end{array}\right]. \tag{5}$$

When $\alpha=1$ and $\beta=2$, Equation (4) collapses to the Gaussian form in Equation (3). However, the solution to Equation (4) can be more succinctly written by performing a Fourier transform in space ($P(x,t)\to p(k,t)$) to obtain the characteristic function, $$p(k,t) = E_\alpha(-D_{\alpha,\beta}|k|^\beta t^\alpha), \tag{6}$$

where $E_\alpha$ is the single-parameter Mittag-Leffler function. The MLF is a well-behaved function defined as a power series expansion, $$f(z) = E_\alpha(z) = \sum_{k=1}^{\infty} \frac{(z)^k}{\Gamma(\alpha k + 1)}, \tag{7}$$

where the $\Gamma$ function is the generalized form of the factorial function, defined for real numbers. When $\alpha=1$ and $\beta=2$, Equation (6) collapses to an exponential function in the Gaussian form with respect to k, $$p(k,t) = \exp(-D_{1,2}|k|^2 t). \tag{8}$$

When $\alpha=1$ and $0<\beta<2$, Equation (6) returns a stretched exponential function with respect to k, $$p(k,t) = \exp(-D_{1,\beta}|k|^\beta t). \tag{9}$$

When $0<\alpha<1$ and $\beta=2$, Equation (6) returns a stretched Mittag-Leffler function with respect to t, $$p(k,t) = E_\alpha(-D_{\alpha,2}|k|^2 t^\alpha). \tag{10}$$

In the most general case of the solution to the diffusion equation shown in Equation (6), the effective diffusion coefficient, $D_{\alpha,\beta}$, has units of $space^\beta/time^\alpha$. In order to formulate Equation (6) such that the diffusion coefficient can be written as $D_{1,2}$ with units of $space^2/time$, parameters $\mu$ (space) and $\tau$ (time) may be inserted to give, $$p(k,t) = E_\alpha\left(-D_{1,2}\frac{\tau^{1-\alpha}}{\mu^{2-\beta}}|k|^\beta t^\alpha\right), \tag{11}$$

such that, $$D_{\alpha,\beta} = D_{1,2}\frac{\tau^{1-\alpha}}{\mu^{2-\beta}}. \tag{12}$$

As $\alpha\to 1$ and $\beta\to 2$, the term $(\tau^{1-\alpha}/\mu^{2-\beta})\to 1$, and, that is to show Equation (11) returns the Gaussian form in Equation (8). The parameters, $\mu$ and $\tau$, are needed as an empirical solution to preserve the units for the diffusion coefficient, however, others have derived analogs to these parameters (i.e., $\Delta x$, $\Delta t$) in conservation of mass problems and heavy tailed limit convergence of fractal and fractional dynamics.

From CTRW to Diffusion-Weighted MRI

In spin-echo diffusion MRI experiments, the signal decay, S, is modeled with a mono-exponential as, $$S/S_0 = \exp(-bD), \tag{13}$$

where b is the product of the q-space and diffusion time terms, $b=q^2(\Delta-\delta/3)$. For brevity, the term $\bar{\Delta}=(\Delta-\delta/3)$ may be defined. As such, a diffusion-weighted experiment can be constructed with a set of b-values, with arbitrary weighting on the q and $\bar{\Delta}$ components, so that a choice can be made to fix $\bar{\Delta}$ and vary q in an array, or to fix q and vary $\bar{\Delta}$ in an array.

A stretched exponential can be fit to data obtained in fixed $\Delta$, varying q experiments with a $\mu$ exponent and in fixed q, varying $\bar{\Delta}$ experiments with an a exponent as an approach to independently interrogate fractional space and fractional time diffusion features. Expanding upon this, the generalized solution to the diffusion equation from CTRW theory in Equations (6) and (11) for modeling anomalous diffusion in MRI can be recast as, $$p(q, \bar{\Delta}) = E_\alpha\left(-D_{1,2}\frac{\tau^{1-\alpha}}{\mu^{2-\beta}}|q|^\beta \bar{\Delta}^\alpha\right), \tag{14}$$

where β absorbs the square of the q term to operate as 0<≤2. An entropy measure can additionally be used as a method to compare and contrast diffusion processes.

From Diffusion-Weighted MRI to Entropy in b-Space

In information theory, the amount of uncertainty in a discrete probability density function, P(x) can be measured with, $$H_x = -\Sigma_{i=1}^N P(x_i)\ln(P(x_i)), \tag{15}$$

where $H_x$ is the Shannon information entropy. Consideration of information formulated in the context of statistical uncertainty provides a tool to compare systems governed by differing stochastic processes. For example, when comparing two α-stable distributions, the Gaussian and the Cauchy, normalized with the same full-width, half maximum values, the Cauchy distribution can be shown to have greater information entropy. Non-Gaussian, or anomalous, diffusion phenomena have been correlated to regions of increased tissue complexity, like the white matter in the brain, which is relatively more anisotropic, heterogeneous, and tortuous compared to gray matter regions. From the information theory perspective, the white matter regions can be considered to have greater entropy than the gray matter regions as they are governed by more uncertain diffusion pdfs.

Another approach to measure the uncertainty in a system is to analyze the characteristic function in terms of the Fourier transform in space (P(x,t)→p(k,t)) with spectral entropy, $$H_k = -\sum_{i=1}^N \frac{\hat{p}(k_i)\ln(\hat{p}(k_i))}{\ln(N)}, \tag{16}$$

where $\hat{p}(k_i) = p(k_i)p^*(k_i)$ reflects the individual wavenumber's contribution to a normalized power spectrum of the Fourier transform, p(k), and the term, ln(N) (i.e., discrete uniform distribution of N samples), is a normalization factor applied so that the spectral entropy, $H_k$, is between 0 and 1.

Furthermore, as Equation (16) is generally defined to measure the uncertainty of a characteristic function, we can adapt this formalism for b-value diffusion decay signals as a function of q and $\bar{\Delta}$, $$H(q, \bar{\Delta}) = -\sum_{i=1}^N \frac{\hat{p}(k_i, \bar{\Delta})\ln(\hat{p}(k_i, \bar{\Delta}))}{\ln(N)}. \tag{17}$$

By inserting the characteristic function in Equation (14) (or, any definition of the characteristic function) into Equation (17), the entropy in the diffusion process can be measured.

4. Example Procedure

To evaluate the MLF parameters in Equation (14) and the entropy, H(q, $\bar{\Delta}$), defined in Equation (17) as potential biomarkers for biological tissue features, demonstration diffusion-weighted MRI measurements were carried out to investigate the effects of arraying q vs. arraying Δ on one healthy fixed rat brain. The outcomes of this demonstration study can serve as a guide for the experimental setup of other studies, such as an inter-subject study on samples of healthy and epileptic fixed rat brains, as well as for diagnostic application of DWI. As the scope of this demonstration study was to investigate the effects of experimental setup on observed diffusion processes within the same biological tissue, one diffusion-weighted gradient direction was used. The y-axis diffusion weighting direction was chosen to evaluate the possibility of anomalous diffusion dynamics along the principal fiber direction of the corpus callosum. The effects of the diffusion weighting direction on the parameter values can be investigated in future studies to evaluate correlations to tensor metrics (e.g., first eigenvalue and fractional anisotropy).

Overnight, prior to imaging experiments, the rat brain was soaked in phosphate buffered saline. For the imaging experiment, the rat brain was placed in a 20 mm imaging tube, and the tube was filled with Fluorinert and secured with a magnetic susceptibility-matched plug to minimize vibrational movement due to the pulsed gradients. The rat brain was oriented in the spectrometer such that the anterior-posterior aligned with the main B0 field (z-axis), the superior-inferior with x-axis, and the lateral with the y-axis. At the Advanced Magnetic Resonance Imaging and Spectroscopy (AMRIS) Facility (Gainesville, Fla.), pulsed gradient stimulated echo (PGSTE) diffusion-weighted experiments were performed on a Bruker spectrometer at 750 MHz (17.6 Tesla, 89 mm bore) with the following parameters: TR=2 s, TE=28 ms, b-values up to 25,000 s/mm$^2$, δ=3.5 ms, NA=2, y-axis diffusion weighting, 1 central slice in the y-z plane, slice thickness=1 mm, FOV=27×18 mm, matrix size of 142×94 pixels, in-plane resolution of 190 μm. It should be highlighted that in all experiments, δ<<Δ to ensure the short-pulse approximation remained valid. Variable TR data (TE=12.5 ms, TR=300-3600 ms, increments of 300 ms) were collected to correct the PGSTE data for T1 relaxation effects. Additionally, the PGSTE data was Rician noise corrected.

Two constant Δ, variable q experiments were performed with Δ fixed at 17.5 and 50 ms. Two constant q, variable Δ experiments were performed with gradient strengths ($g_y$) at 350 and 525 mT/m to achieve q-values of 52 and 78 mm$^{-1}$, respectively. For the constant Δ=17.5 ms experiment, q was arrayed at 0, 39.7, 55.5, 67.7, 95.4, 116.7, 134.7, 150.5, 164.9, 178.1, and 190.3 mm$^{-1}$. For the constant Δ=50 ms experiment, q was arrayed at 0, 24.9, 33.8, 40.9, 57.0, 69.4, 79.9, 89.2, 97.7, 105.4, 112.4 mm$^{-1}$. For the constant q=78 mm$^{-1}$ experiment, Δ was arrayed at 17.5, 31.5, 45.5, 59.5, 73.5, 87.5, 101.5, 108.5, and 115 ms. For the constant q=52 mm$^{-1}$ experiment, Δ was arrayed at 17.5, 51.5, 85.5, 119.5, 153.5, 187.5, 221.5, 238.5, and 250 ms.

Because the generalized diffusion model in Equation (14) specifies $D_{1,2}$, μ, and τ as a ratio, any number of parameter value combinations can satisfy successful fitting results. To constrain these parameters, $D_{1,2}$, μ, and τ were first estimated using intermediate fits. To estimate the diffusion coefficient, a mono-exponential function was fit to the first 3 low b-value samples, referred to as, $D_m$ above. After $D_m$ estimation, two analogous stretched exponential fitting procedures were used to fit the constant $\bar{\Delta}$ and constant q experimental data in order to find estimates of $\bar{\tau}$ and $\bar{\mu}$ using, as discussed above in and illustrated in FIGS. 1 and 2.

Following the intermediate parameter estimations, $D_m$, $\bar{\tau}$, $\bar{\mu}$, α=1, β=2 were used as starting values in the non-linear least squared fit of the Mittag-Leffler function in order to converge upon $D_{1,2}$, μ, and τ, α, and β values. $D_{1,2}$, μ, and τ were allowed to float ±50% from their initial estimates. The value for ac was bounded between 0 and 1.1 and β between 0 and 2.2.

After the MLF parameters were determined, the characteristic decay curve for p(q, $\bar{\Delta}$) was constructed using N=1,500 increments arrayed over variable q or variable $\bar{\Delta}$ for b-values between 0 and 25,000 s/mm². Then, the entropy (defined in Equation (17)) in the diffusion process, as modeled by the MLF, was computed as H(q, $\bar{\Delta}$)$_{MLF}$. For comparison, using the mono-exponential model ($D_m$) in Equation (13), a characteristic decay curve of N=1,500 increments arrayed over b-values between 0 and 25,000 s/mm² was constructed. The entropy in the diffusion process, as modeled by the mono-exponential function, was computed as H(q, $\bar{\Delta}$)$_{mono}$.

Results of the above procedure are discussed above in connection with Tables 1-4 and FIGS. 1-6.

An example embodiment of the present invention has been described above. Those skilled in the art will understand, however, that changes and modifications can be made to this embodiment without departing from the true scope and spirit of the invention, which is defined by the claims.

What is claimed:

1. A computer-implemented method for characterizing a biological structure, the method comprising:
    acquiring a first set of diffusion weighted magnetic resonance imaging (DWI) data of biologic material, the first set of DWI data having been measured by a magnetic resonance imaging (MRI) system using a fixed diffusion encoding gradient and a plurality of diffusion time resolutions;
    acquiring a second set of DWI data of the biologic material, the second set of DWI data having been measured by the MRI system using a fixed diffusion time resolution and a plurality of diffusion encoding gradients;
    analytically fitting the first and second sets of DWI data with a fractional power-law diffusion model parameterized by fractional exponents each uniquely corresponding to one of a plurality of bio-markers of the biologic material;
    determining values of the fractional exponents from the analytical fitting of the first and second sets of DWI data; and
    generating and displaying at least one image of the biologic material as represented by at least one of the plurality of bio-markers based on the determined values of the uniquely corresponding fractional exponent,
    wherein the fractional power-law diffusion model includes a mean square displacement (MSD) of a power-law form $\langle x^2(t)\rangle \sim t^{2\alpha/\beta}$ that derives from a random walk (RW) model having stochastic processes for jump-length distance and time between jumps, the stochastic processes having independent probability density functions (pdfs),
    wherein x is a distance measure and t is time,
    wherein α and β are parameters of the model corresponding to two of the bio-markers,
    wherein the diffusion spatial resolution is represented by q, and the diffusion temporal resolution is represented by Δ,
    and wherein the method further comprises determining an entropy H(q, Δ) as a measure of uncertainty in the pdfs, the entropy H(q, Δ) being another of the bio-markers.

2. The method of claim 1, wherein acquiring the first set of DWI data of the biologic material comprises acquiring the first set of DWI data from DWI data previously measured and provided for storage by the MRI system,
    and wherein acquiring the second set of DWI data of the biologic material comprises acquiring the first set of DWI data from the DWI data previously measured and provided for storage by the MRI system.

3. The method of claim 1, wherein the fixed diffusion encoding gradient and the plurality of diffusion time resolutions comprises:
    a diffusion spatial resolution with a value fixed in a range of 15 mm⁻¹-100 mm⁻¹, and corresponding to a range of gradient strengths of 100 mT/m-1000 mT/m; and
    an array of diffusion temporal resolution values in a range of 15 ms-250 ms.

4. The method of claim 1, wherein the fixed diffusion time resolution and the plurality of diffusion encoding gradients comprises:
    a diffusion temporal resolution with a value fixed in a range of 15 ms-100 ms; and
    an array of diffusion spatial resolution values a range of 0 mm⁻¹-200 mm⁻¹, and corresponding to a range of gradient strengths of 0 mT/m-1500 mT/m.

5. The method of claim 1, wherein the fractional power-law diffusion model has a solution expressed analytically as:

$$E_\alpha\left(\frac{D_{1,2}\tau^{1-\alpha}}{\mu^{2-\beta}}q^\beta\Delta^\alpha\right),$$

wherein μ and τ are two further model parameters corresponding to a further two of the bio-markers,
    wherein $D_{1,2}$ is a measurable diffusion coefficient corresponding to an additional one of the bio-markers,
    wherein $E_\alpha$ is a Mittag-Leffler function (MLF),
    wherein a mono-exponential model of signal decay in DWI is expressed analytically as:

$$\frac{S}{S_0} = \exp(-bD),$$

wherein a stretched exponential model of signal decay in DWI is expressed analytically as:

$$\frac{S}{S_0} = \exp[-(bD)^w],$$

wherein $S_0$ is an initial signal and S is a decaying signal,
    wherein b=q²(Δ-δ/3), δ is a pulse signal duration, and D is a classical diffusion coefficient,
    wherein w is a stretching parameter,
    and wherein analytically fitting the first and second sets of DWI data with the fractional power-law diffusion model comprises:
    determining an estimated measurable diffusion coefficient $D_m$ by analytically fitting a subset of the first and second sets of DWI data with the mono-exponential model of signal decay;
    determining estimated values of μ and τ, $\bar{\mu}$ and $\bar{\tau}$, respectively, by (i) analytically fitting the first set of DWI data with the stretched exponential model of signal decay and w=α, and (ii) analytically fitting the second set of DWI data with the stretched exponential model of signal decay and w=β; and determining $D_{1,2}$, $\alpha$, $\beta$, $\mu$, and $\tau$ by iteratively fitting the first and second sets of DWI data with the fractional power-law diffusion model using $D_m$, $\bar{\mu}$, $\bar{\tau}$, $\alpha=1$, and $\beta=2$ as starting values.

6. The method of claim 1, wherein the biologic material comprises a human brain.

7. In a magnetic resonance imaging (MRI) system, a method for characterizing a biological structure, the method comprising:
  acquiring a first set of diffusion weighted MRI (DWI) data of biologic material with the MIll system using a fixed diffusion encoding gradient and a plurality of diffusion time resolutions;
  acquiring a second set of DWI data of the biologic material with the MIll system using a fixed diffusion time resolution and a plurality of diffusion encoding gradients;
  analytically fitting the first and second sets of DWI data with a fractional power-law diffusion model parameterized by fractional exponents each uniquely corresponding to one of a plurality of bio-markers of the biologic material;
  determining values of the fractional exponents from the analytical fitting of the first and second sets of DWI data; and
  generating and displaying at least one image of the biologic material as represented by at least one of the plurality of bio-markers based on the determined values of the uniquely corresponding fractional exponent,
  wherein the fractional power-law diffusion model includes a mean square displacement (MSD) of a power-law form $<x^2(t)> \sim t^{2\alpha/\beta}$ that derives from a random walk (RW) model having stochastic processes for jump-length distance and time between jumps, the stochastic processes having independent probability density functions (pdfs),
  wherein x is a distance measure and t is time,
  wherein $\alpha$ and $\beta$ are parameters of the model corresponding to two of the bio-markers,
  wherein the diffusion spatial resolution is represented by q, and the diffusion temporal resolution is represented by $\Delta$,
  and wherein the method further comprises determining an entropy $H(q, \Delta)$ as a measure of uncertainty in the pdfs, the entropy $H(q, \Delta)$ being another of the bio-markers.

8. The method of claim 7, wherein the biologic material comprises a human brain.

9. A system comprising:
  one or more processors;
  memory; and
  machine-readable instructions stored in the memory that, when executed by the one or more processors, cause the system to carry out functions including:
  acquiring a first set of diffusion weighted magnetic resonance imaging (DWI) data of biologic material, wherein the first set of DWI data comprise measurements made by a magnetic resonance imaging (MRI) system using a fixed diffusion encoding gradient and a plurality of diffusion time resolutions;
  acquiring a second set of DWI data of the biologic material, wherein the second set of DWI data comprise measurements made by the MRI system using a fixed diffusion time resolution and a plurality of diffusion encoding gradients;
  analytically fitting the first and second sets of DWI data with a fractional power-law diffusion model parameterized by fractional exponents each uniquely corresponding to one of a plurality of bio-markers of the biologic material;
  determining values of the fractional exponents from the analytical fitting of the first and second sets of DWI data; and
  generating and displaying at least one image of the biologic material as represented by at least one of the plurality of bio-markers based on the determined values of the uniquely corresponding fractional exponent,
  wherein the fractional power-law diffusion model includes a mean square displacement (MSD) of a power-law form $<x^2(t)> \sim t^{2\alpha/\beta}$ that derives from a random walk (RW) model having stochastic processes for jump-length distance and time between jumps, the stochastic processes having independent probability density functions (pdfs),
  wherein x is a distance measure and t is time,
  wherein $\alpha$ and $\beta$ are parameters of the model corresponding to two of the bio-markers,
  wherein the diffusion spatial resolution is represented by q, and the diffusion temporal resolution is represented by $\Delta$,
  and wherein the method further comprises determining an entropy $H(q, \Delta)$ as a measure of uncertainty in the pdfs, the entropy $H(q, \Delta)$ being another of the bio-markers.

10. The system of claim 9, wherein acquiring the first set of DWI data of the biologic material comprises acquiring the first set of DWI data from DWI data previously measured and provided for storage by the MRI system,
  and wherein acquiring the second set of DWI data of the biologic material comprises acquiring the first set of DWI data from the DWI data previously measured and provided for storage by the MRI system.

11. The system of claim 9, wherein the fixed diffusion encoding gradient and the plurality of diffusion time resolutions comprises:
  a diffusion spatial resolution with a value fixed in a range of 15 mm$^{-1}$–100 mm$^{-1}$, and corresponding to a range of gradient strengths of 100 mT/m-1000 mT/m; and
  an array of diffusion temporal resolution values in a range of 15 ms-250 ms.

12. The system of claim 9, wherein the fixed diffusion time resolution and the plurality of diffusion encoding gradients comprises:
  a diffusion temporal resolution with a value fixed in a range of 15 ms-100 ms; and
  an array of diffusion spatial resolution values a range of 0 mm$^{-1}$-200 mm$^{-1}$, and corresponding to a range of gradient strengths of 0 mT/m-1500 mT/m.

13. The system of claim 9, wherein the fractional power-law diffusion model has a solution expressed analytically as:

$$E_\alpha\left(\frac{D_{1,2}\tau^{1-\alpha}}{\mu^{2-\beta}}q^\beta\Delta^\alpha\right),$$

wherein $\mu$ and $\tau$ are two further model parameters corresponding to a further two of the bio-markers,
wherein $D_{1,2}$ is a measurable diffusion coefficient corresponding to an additional one of the bio-markers,
wherein $E_\alpha$ is a Mittag-Leffler function (MLF),
wherein a mono-exponential model of signal decay in DWI is expressed analytically as:

$$\frac{S}{S_0} = \exp(-bD),$$

wherein a stretched exponential model of signal decay in DWI is expressed analytically as:

$$\frac{S}{S_0} = \exp[-(bD)^w],$$

wherein $S_0$ is an initial signal and S is a decaying signal,
wherein $b=q^2(\Delta-\delta/3)$, $\delta$ is a pulse signal duration, and D is a classical diffusion coefficient,
wherein w is a stretching parameter,
and wherein analytically fitting the first and second sets of DWI data with the fractional power-law diffusion model comprises:
determining an estimated measurable diffusion coefficient $D_m$ by analytically fitting a subset of the first and second sets of DWI data with the mono-exponential model of signal decay;
determining estimated values of $\mu$ and $\tau$, $\bar{\mu}$ and $\bar{\tau}$, respectively, by (i) analytically fitting the first set of DWI data with the stretched exponential model of signal decay and $w=\alpha$, and (ii) analytically fitting the second set of DWI data with the stretched exponential model of signal decay and $w=\beta$; and
determining $D_{1,2}$, $\alpha$, $\beta$, $\mu$, and $\tau$ by iteratively fitting the first and second sets of DWI data with the fractional power-law diffusion model using $D_m$, $\bar{\mu}$, $\bar{\tau}$, $\alpha=1$, and $\beta=2$ as starting values.

14. The system of claim 9, wherein the biologic material comprises a human brain.

15. A magnetic resonance imaging (MRI) system comprising:
one or more processors;
memory;
a main magnet;
one or more gradient coils; and
machine-readable instructions stored in the memory that, when executed by the one or more processors, cause the MRI system to carry out functions including:
acquiring a first set of diffusion weighted MRI (DWI) data of biologic material in the MRI system using a fixed diffusion encoding gradient and a plurality of diffusion time resolutions,
acquiring a second set of DWI data of the biologic material in the MRI system using a fixed diffusion time resolution and a plurality of diffusion encoding gradients;
analytically fitting the first and second sets of DWI data with a fractional power-law diffusion model parameterized by fractional exponents each uniquely corresponding to one of a plurality of bio-markers of the biologic material,
determining values of the fractional exponents from the analytical fitting of the first and second sets of DWI data, and
generating and displaying at least one image of the biologic material as represented by at least one of the plurality of bio-markers based on the determined values of the uniquely corresponding fractional exponent,
wherein the fractional power-law diffusion model includes a mean square displacement (MSD) of a power-law form $\langle x^2(t)\rangle \sim t^{2\alpha/\beta}$ that derives from a random walk (RW) model having stochastic processes for jump-length distance and time between jumps, the stochastic processes having independent probability density functions (pdfs),
wherein x is a distance measure and t is time,
wherein $\alpha$ and $\beta$ are parameters of the model corresponding to two of the bio-markers,
wherein the diffusion spatial resolution is represented by q, and the diffusion temporal resolution is represented by $\Delta$,
and wherein the method further comprises determining an entropy $H(q, \Delta)$ as a measure of uncertainty in the pdfs, the entropy $H(q, \Delta)$ being another of the bio-markers.

16. The MRI system of claim 15, wherein the biologic material comprises a human brain.

* * * * *